United States Patent
Raptis et al.

(10) Patent No.: US 9,615,792 B2
(45) Date of Patent: Apr. 11, 2017

(54) SYSTEM AND METHOD FOR CONSERVING BATTERY POWER IN A PATIENT MONITORING SYSTEM

(75) Inventors: Mark Raptis, Valley Center, CA (US); Amir Jafri, San Diego, CA (US); Alison Burdett, Oxford (GB); Ganesh Kathiresan, Osterley (GB)

(73) Assignee: CAREFUSION 303, INC., San Diego, CA (US)

( * ) Notice: Subject to any disclaimer, the term of this patent is extended or adjusted under 35 U.S.C. 154(b) by 1109 days.

(21) Appl. No.: 12/844,796

(22) Filed: Jul. 27, 2010

(65) Prior Publication Data
US 2012/0029315 A1 Feb. 2, 2012

(51) Int. Cl.
G08C 19/22 (2006.01)
H04Q 9/00 (2006.01)
G08C 19/16 (2006.01)
A61B 5/04 (2006.01)
A61B 5/00 (2006.01)

(52) U.S. Cl.
CPC .......... *A61B 5/6833* (2013.01); *A61B 5/0022* (2013.01); *A61B 2560/0209* (2013.01)

(58) Field of Classification Search
None
See application file for complete search history.

(56) References Cited

U.S. PATENT DOCUMENTS

| | | |
|---|---|---|
| 3,677,261 A | 7/1972 | Day |
| 3,830,224 A | 8/1974 | Vanzetti et al. |
| 4,121,574 A | 10/1978 | Lester |
| 4,396,020 A | 8/1983 | Wolff et al. |
| 4,407,295 A | 10/1983 | Steuer et al. |
| 4,490,005 A | 12/1984 | Hovey |
| 4,530,366 A | 7/1985 | Nessi et al. |
| 4,541,734 A | 9/1985 | Ishizaka |
| 4,686,998 A | 8/1987 | Robbins |
| 4,708,146 A | 11/1987 | Lane |
| 4,765,340 A | 8/1988 | Sakai et al. |
| 4,838,273 A | 6/1989 | Cartmell |
| 4,967,765 A | 11/1990 | Turner et al. |

(Continued)

FOREIGN PATENT DOCUMENTS

| | | |
|---|---|---|
| JP | 61003019 | 1/1986 |
| JP | 2002-507131 | 3/2002 |

(Continued)

OTHER PUBLICATIONS

Akyldiz, I.F. et al.; "Wireless Multimedia Sensor Networks: A survey." IEEE Wireless Communications. Dec. 2007, p. 32-39.

(Continued)

*Primary Examiner* — Firmin Backer
*Assistant Examiner* — Jerold Murphy
(74) *Attorney, Agent, or Firm* — McDermott Will & Emery LLP (57) ABSTRACT

A vital-signs patch in a patient monitoring system is disclosed. The patch includes a housing configured to be attached to the skin of a patient, the housing containing a radio that can selectably transmit and receive on more than one frequency and a processor. The processor configures the radio to transmit and receive on a determined frequency based at least in part on the level of noise detected on the frequencies.

13 Claims, 6 Drawing Sheets

(56) References Cited

U.S. PATENT DOCUMENTS

| | | |
|---|---|---|
| 5,050,612 A | 9/1991 | Matsumura |
| 5,094,545 A | 3/1992 | Larsson et al. |
| 5,153,584 A | 10/1992 | Engira |
| 5,258,577 A | 11/1993 | Clements |
| 5,273,036 A | 12/1993 | Kronberg et al. |
| 5,344,335 A | 9/1994 | Scholz et al. |
| 5,353,793 A | 10/1994 | Bornn |
| 5,401,100 A | 3/1995 | Thackston et al. |
| 5,511,553 A | 4/1996 | Segalowitz |
| 5,544,661 A | 8/1996 | Davis et al. |
| 5,803,915 A | 9/1998 | Kremenchugsky et al. |
| 5,980,467 A | 11/1999 | Henry |
| 6,030,342 A | 2/2000 | Amano et al. |
| 6,042,966 A | 3/2000 | Cheu |
| 6,222,456 B1 | 4/2001 | Tice |
| 6,270,252 B1 | 8/2001 | Siefert |
| 6,273,886 B1 | 8/2001 | Edwards et al. |
| 6,287,252 B1 | 9/2001 | Lugo |
| 6,324,426 B1 | 11/2001 | Thompson |
| 6,355,031 B1 | 3/2002 | Edwards et al. |
| 6,358,245 B1 | 3/2002 | Edwards et al. |
| 6,454,708 B1 | 9/2002 | Ferguson et al. |
| 6,468,261 B1 | 10/2002 | Small et al. |
| 6,494,829 B1 | 12/2002 | New, Jr. et al. |
| 6,517,497 B2 | 2/2003 | Rymut et al. |
| 6,636,754 B1 | 10/2003 | Baura et al. |
| 6,740,059 B2 | 5/2004 | Flaherty |
| 6,950,688 B2 | 9/2005 | Axelgaard et al. |
| 6,963,772 B2 | 11/2005 | Bloom et al. |
| 6,980,112 B2 | 12/2005 | Nee |
| 7,052,472 B1 | 5/2006 | Miller et al. |
| 7,061,858 B1 | 6/2006 | Di Benedetto et al. |
| 7,198,600 B2 | 4/2007 | Tamaki et al. |
| 7,319,895 B2 | 1/2008 | Klefstad-Sillonville et al. |
| 7,355,512 B1 | 4/2008 | Al-Ali |
| RE40,470 E | 8/2008 | Fitzpatrick et al. |
| 7,434,991 B2 | 10/2008 | Harr et al. |
| 7,447,526 B2 | 11/2008 | Kim et al. |
| 7,542,437 B1 | 6/2009 | Redi et al. |
| 7,639,652 B1 | 12/2009 | Amis et al. |
| 7,645,263 B2 | 1/2010 | Angel et al. |
| 7,668,588 B2 | 2/2010 | Kovacs |
| 7,924,150 B2 | 4/2011 | Baldus et al. |
| 7,959,574 B2 | 6/2011 | Bardy |
| 7,962,188 B2 | 6/2011 | Kiani et al. |
| 8,007,436 B2 | 8/2011 | Katayama |
| 8,200,320 B2 | 6/2012 | Kovacs |
| 8,228,188 B2 | 7/2012 | Key et al. |
| 8,506,480 B2 | 8/2013 | Banet et al. |
| 8,721,562 B2 | 5/2014 | Abreu |
| 2001/0047127 A1 | 11/2001 | New, Jr. et al. |
| 2002/0007676 A1 | 1/2002 | Ward et al. |
| 2002/0013538 A1 | 1/2002 | Teller |
| 2002/0045836 A1* | 4/2002 | Alkawwas ............... 600/509 |
| 2002/0099277 A1 | 7/2002 | Harry et al. |
| 2002/0107436 A1 | 8/2002 | Barton et al. |
| 2002/0109621 A1* | 8/2002 | Khair et al. ............ 341/174 |
| 2002/0198519 A1 | 12/2002 | Qin et al. |
| 2003/0004403 A1 | 1/2003 | Drinan et al. |
| 2003/0040305 A1* | 2/2003 | Ng et al. ................ 455/419 |
| 2003/0069510 A1 | 4/2003 | Semler |
| 2003/0191445 A1 | 10/2003 | Wallen et al. |
| 2003/0212319 A1 | 11/2003 | Magill |
| 2003/0212340 A1 | 11/2003 | Lussier et al. |
| 2003/0229809 A1 | 12/2003 | Wexler et al. |
| 2004/0015058 A1 | 1/2004 | Besson et al. |
| 2004/0030259 A1 | 2/2004 | Dae et al. |
| 2004/0062133 A1* | 4/2004 | Tsuji ...................... 365/232 |
| 2004/0116822 A1 | 6/2004 | Lindsey |
| 2004/0165646 A1 | 8/2004 | Shidemantle et al. |
| 2004/0215098 A1 | 10/2004 | Barton et al. |
| 2004/0220538 A1 | 11/2004 | Panopoulos |
| 2004/0236188 A1 | 11/2004 | Hutchinson et al. |
| 2005/0085706 A1 | 4/2005 | Perrault et al. |
| 2005/0101843 A1 | 5/2005 | Quinn et al. |
| 2005/0131288 A1 | 6/2005 | Turner et al. |
| 2005/0159653 A1 | 7/2005 | Lijima et al. |
| 2005/0195079 A1 | 9/2005 | Cohen |
| 2005/0228297 A1 | 10/2005 | Banet et al. |
| 2005/0228299 A1 | 10/2005 | Banet |
| 2005/0231350 A1 | 10/2005 | Littrell et al. |
| 2005/0245831 A1 | 11/2005 | Banet |
| 2005/0245839 A1 | 11/2005 | Stivoric et al. |
| 2005/0249263 A1 | 11/2005 | Yerlikaya et al. |
| 2005/0251128 A1 | 11/2005 | Amoah |
| 2006/0009697 A1 | 1/2006 | Banet et al. |
| 2006/0045165 A1 | 3/2006 | Chan et al. |
| 2006/0047987 A1 | 3/2006 | Prabhakaran et al. |
| 2006/0094971 A1 | 5/2006 | Drew |
| 2006/0098576 A1 | 5/2006 | Brownrigg et al. |
| 2006/0155183 A1* | 7/2006 | Kroecker et al. ........ 600/391 |
| 2006/0202816 A1 | 9/2006 | Crump et al. |
| 2006/0224349 A1 | 10/2006 | Butterfield |
| 2006/0276714 A1 | 12/2006 | Holt et al. |
| 2007/0032706 A1 | 2/2007 | Kamath et al. |
| 2007/0041424 A1 | 2/2007 | Lev et al. |
| 2007/0099678 A1 | 5/2007 | Kim et al. |
| 2007/0116089 A1 | 5/2007 | Bisch et al. |
| 2007/0123756 A1 | 5/2007 | Kitajima et al. |
| 2007/0129622 A1 | 6/2007 | Bourget et al. |
| 2007/0135866 A1 | 6/2007 | Baker et al. |
| 2007/0142715 A1 | 6/2007 | Banet et al. |
| 2007/0191728 A1 | 8/2007 | Shennib |
| 2007/0208233 A1 | 9/2007 | Kovacs |
| 2007/0219434 A1 | 9/2007 | Abreu |
| 2007/0225614 A1 | 9/2007 | Naghavi et al. |
| 2007/0293781 A1 | 12/2007 | Sims et al. |
| 2008/0042866 A1 | 2/2008 | Morse et al. |
| 2008/0091090 A1 | 4/2008 | Guillory et al. |
| 2008/0097178 A1 | 4/2008 | Banet et al. |
| 2008/0097422 A1 | 4/2008 | Edwards et al. |
| 2008/0114220 A1 | 5/2008 | Banet et al. |
| 2008/0119707 A1 | 5/2008 | Stafford |
| 2008/0143512 A1 | 6/2008 | Wakisaka et al. |
| 2008/0183054 A1 | 7/2008 | Kroeger et al. |
| 2008/0200770 A1 | 8/2008 | Hubinette |
| 2008/0200774 A1 | 8/2008 | Luo |
| 2008/0208026 A1 | 8/2008 | Noujaim et al. |
| 2008/0221399 A1 | 9/2008 | Zhou et al. |
| 2008/0234600 A1 | 9/2008 | Marsh |
| 2008/0275327 A1 | 11/2008 | Faarbaek et al. |
| 2008/0294065 A1 | 11/2008 | Waldhoff et al. |
| 2008/0305154 A1 | 12/2008 | Yanaki |
| 2009/0018409 A1 | 1/2009 | Banet et al. |
| 2009/0054737 A1 | 2/2009 | Magar et al. |
| 2009/0062670 A1 | 3/2009 | Sterling et al. |
| 2009/0069642 A1 | 3/2009 | Gao et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076345 A1 | 3/2009 | Manicka et al. |
| 2009/0076346 A1 | 3/2009 | James et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076405 A1 | 3/2009 | Amurthur et al. |
| 2009/0105549 A1 | 4/2009 | Smith et al. |
| 2009/0105605 A1 | 4/2009 | Abreu |
| 2009/0131759 A1 | 5/2009 | Sims et al. |
| 2009/0131761 A1 | 5/2009 | Sweitzer et al. |
| 2009/0182204 A1* | 7/2009 | Semler et al. ............ 600/301 |
| 2009/0203974 A1 | 8/2009 | Hickle |
| 2009/0227877 A1 | 9/2009 | Tran |
| 2009/0259139 A1 | 10/2009 | Stapien et al. |
| 2009/0270744 A1 | 10/2009 | Prstojevich et al. |
| 2009/0271681 A1 | 10/2009 | Piret et al. |
| 2010/0010319 A1 | 1/2010 | Tivig et al. |
| 2010/0036212 A1 | 2/2010 | Rieth |
| 2010/0056886 A1 | 3/2010 | Hurtubise et al. |
| 2010/0081949 A1 | 4/2010 | Derby, Jr. |
| 2010/0113894 A1 | 5/2010 | Padiy |
| 2010/0121217 A1 | 5/2010 | Padiy et al. |

(56) References Cited

U.S. PATENT DOCUMENTS

| | | |
|---|---|---|
| 2010/0222688 A1 | 9/2010 | Fischell et al. |
| 2010/0234716 A1 | 9/2010 | Engel |
| 2010/0292605 A1 | 11/2010 | Grassl et al. |
| 2010/0298656 A1 | 11/2010 | McCombie et al. |
| 2010/0298895 A1 | 11/2010 | Ghaffari et al. |
| 2010/0323634 A1 | 12/2010 | Kimura |
| 2010/0324548 A1 | 12/2010 | Godara et al. |
| 2011/0004076 A1 | 1/2011 | Janna et al. |
| 2011/0060252 A1 | 3/2011 | Simonsen et al. |
| 2011/0066062 A1 | 3/2011 | Banet et al. |
| 2011/0144470 A1 | 6/2011 | Mazar et al. |
| 2011/0160601 A1 | 6/2011 | Wang et al. |
| 2011/0176465 A1 | 7/2011 | Panta et al. |
| 2011/0182213 A1 | 7/2011 | Forssell et al. |
| 2011/0224557 A1 | 9/2011 | Banet et al. |
| 2012/0029300 A1 | 2/2012 | Paquet |
| 2012/0029308 A1 | 2/2012 | Paquet |
| 2012/0029314 A1 | 2/2012 | Paquet et al. |
| 2012/0108920 A1 | 5/2012 | Bly et al. |
| 2012/0165621 A1 | 6/2012 | Grayzel et al. |
| 2012/0238901 A1 | 9/2012 | Augustine |

FOREIGN PATENT DOCUMENTS

| | | |
|---|---|---|
| JP | 2004-503266 | 2/2004 |
| JP | 2005-521453 | 7/2005 |
| JP | 2009-544065 | 12/2009 |
| KR | 20070097725 | 10/2007 |

OTHER PUBLICATIONS

Arisha, K. et al. "System-Level Power Optimization for wireless Multimedia Communication." Editors: Ramesh K. and Goodman, D.; Springer US; 2002, p. 21-40.
Cardei, M. et al.; "Improving Wireless Sensor Network Lifetime through Power Aware Organization"; Wireless Networks 11, 222-240. 2005.
Davidson K. G. et al., "Measurement of tidal volume by using transthoracic impedance variations in rats," J. Appl. Physiol. 86:759-766, 1999.
Ernst. J.M. et al, "Impedance Penumography: noise as signal in impedance cardiography," Psychophysiology, 36 (1999) 333-338.
Freundlich J.J. et al., Electrical Impedence Pneumography for Simple Nonrestrictive Continuous Monitoring of Respiratory Rate, Rhythm and Tidal Volume for Surgical Patients, Chest, 65, p. 181-184, 1974.
Herman, T. et al.; "A Distributed TDMA Slot Assignment Algorithm for Wireless Sensor Networks"; S. Nikoletseas and J. Rolim (Eds.): Algosensors 2004, LNCS 3121, pp. 45-58, 2004, Springer-Verlag Berlin Heidelberg 2004.
Hohlt, B. et al. "Flexible Power Scheduling for Sensor Networks," IPSN'04, Apr. 26-27, 2004, Berkeley, California, USA. p. 1-10.
Kelkar, S. P. et al., "Development of Movement artifact free breathing monitor," J. Instrum. Soc. India 38(1) 34-43, 2008.
Lee, W. L.; "Flexible-Schedule-Based TDMA Protocol for Fault-Tolerant and Energy-Efficient Wireless Sensor Networks," IEEE Transactions on Parallel and Distributed Systems, vol. 19, No. 6, Jun. 2008; p. 851-864.
Lee, W. L.; "Flexible-Schedule-Based TDMA Protocols for Supporting Fault-Tolerance, On-Demand TDMA Slot Transfer, and Peer-to-Peer Communication in Wireless Sensor Networks;" Thesis for the degree of Doctor in Philosophy, University of Western Australia, 2007, p. 1-213.
Loriga, G., et al., "Textile sensing interfaces for cardiopulmonary signs monitoring," Proceedings of the 2005 IEEE Engineering in Medicine and Biology 27th Annual Conference Shanghai, China, Sep. 1-4, 2005, p. 7349-7352.
Luo, S. et al., "The electrode system in Impedence-Based Ventilation Measurement," IEEE Transactions of biomedical Engineering, vol. 39, No. 11, Nov. 1992, p. 1130-1140.

Matthews, R., et al., "A Wearable Physiological Sensor Suite for Unobtrusive Monitoring of Physiological and Cognitive State," Proceedings of the 29th Annual International Conference of the IEEE EMBS Cite Internationale, Lyon, France, Aug. 23-26, 2007, pp. 1-6.
Pacela, A.F. "Impedance Pneumograph, a survey of instrumentation techniques," Med. & Biol. Engineering, vol. 4, p. 1-5, 1966.
Pantazis, N.A. et al.; "Energy efficiency in wireless sensor networks using sleep mode TDMA scheduling," Ad Hoc Networks 7 (2009) 322-343.
Paradiso, R. et al., "A wearable health care system based on knitted integrated sensors," IEEE transactions on Information Technology in biomedicine, vol. 9, No. 3, Sep. 2005, p. 337-344.
Park, et al., "Development of Flexible Self Adhesive Patch for Professional Heat Stress Monitoring Service," Proceedings of the 2005 IEEE Engineering in Medicine and Biology 27th Annual Conference Shanghai, China, Sep. 1-4, 2005, pp. 3789-3792.
Rashid, R. A. et al; "Development of Energy Aware TDMA-Based MAC Protocol for Wireless Sensor Network System," European Journal of Scientific, vol. 30 No. 4 (2009), pp. 571-578.
Shaw, G.A. et al., "Warfighter Physiological and Environmental Monitoring: A Study for the U.S. Army Research Institute in Environmental Medicine and the Soldier Systems Center," 2004, Lincoln Laboratory, MIT, pp. 1-141.
Zheng, W. W. et al. "Adaptive-frame-based Dynamic Slot Assignment Protocol for Tactical Data Link System," 2009 International Conference of Networks Security, Wireless Communications and Trusted Computing, IEEE, p. 709-714.
Office Action issued in U.S. Appl. No. 12/844,801, dated Aug. 14, 2014.
Office Action issued in U.S. Appl. No. 12/844,794, dated Sep. 26, 2014.
International Preliminary Report on Patentability in International Application No. PCT/US2011/030088, dated Oct. 27, 2012, 13 pages.
International Preliminary Report on Patentability in International Application No. PCT/US2011/045240, dated Jan. 29, 2013, 6 pages.
International Preliminary Report on Patentability in International Application No. PCT/US2011/045245, dated Jan. 29, 2013, 5 pages.
International Preliminary Report on Patentability in International Application No. PCT/US2011/045249, dated Jan. 29, 2013, 4 pages.
International Preliminary Report on Patentability in International Application No. PCT/US2011/045256, dated Jan. 29, 2013, 4 pages.
International Preliminary Report on Patentability in International Application No. PCT/US2011/045258, dated Jan. 29, 2013, 5 pages.
International Preliminary Report on Patentability in International Application No. PCT/US2011/045337, dated Jan. 9, 2013, 4 pages.
International Preliminary Report on Patentability in International Application No. PCT/US2011/045361, dated Jan. 29, 2013, 6 pages.
International Preliminary Report on Patentability in International Application No. PCT/US2011/045408, dated Jan. 29, 2013, 4 pages.
International Preliminary Report on Patentability in International Application No. PCT/US2011/045414, dated Jan. 29, 2013, 6 pages.
International Preliminary Report on Patentability in International Application No. PCT/US2011/045415, dated Jan. 29, 2013, 4 pages.
International Preliminary Report on Patentability in International Application No. PCT/US2011/045419, dated Jan. 29, 2013, 5 pages.
International Preliminary Report on Patentability in International Application No. PCT/US2011/045425, dated Jan. 29, 2013, 5 pages.
International Search Report and Written Opinion for International Application No. PCT/US2011/045408, dated Feb. 24, 2012, 6 pages.
International Search Report and Written Opinion in International Application No. PCT/US2011/045361, dated Apr. 6, 2012, 8 pages.
International Search Report and Written Opinion in International Application No. PCT/US2011/030088, dated Oct. 31, 2011, 7 pages.
International Search Report and Written Opinion in International Application No. PCT/US2011/045240, dated Mar. 15, 2012, 8 pages.
International Search Report and Written Opinion in International Application No. PCT/US2011/045245, dated Mar. 28, 2012, 7 pages.

(56) References Cited

OTHER PUBLICATIONS

International Search Report and Written Opinion in International Application No. PCT/US2011/045249, dated Mar. 12, 2012, 6 pages.
International Search Report and Written Opinion in International Application No. PCT/US2011/045256, dated Feb. 9, 2012, 12 pages.
International Search Report and Written Opinion in International Application No. PCT/US2011/045258, dated Apr. 6, 2012, 12 pages.
International Search Report and Written Opinion in International Application No. PCT/US2011/045337, dated Feb. 9, 2012, 7 pages.
International Search Report and Written Opinion in International Application No. PCT/US2011/045414, dated Feb. 24, 2012, 9 pages.
International Search Report and Written Opinion in International Application No. PCT/US2011/045415, dated Feb. 24, 2012, 7 pages.
International Search Report and Written Opinion in International Application No. PCT/US2011/045419, dated Apr. 6, 2012, 7 pages.
International Search Report and Written Opinion in International Application No. PCT/US2011/045425, dated Apr. 6, 2012, 7 pages.
Kessler, "TCP/IP and tcpdump Pocket reference Guide", Champlain College, 2006.
Zhihui Chen; Kohkhar, A. "Self organization and energy efficient TDMA MAC protocol by wake up for wireless sensor networks," Sensor and Ad Hoc Communications and Networks, 2004. IEEE SECON 2004. 2004 First Annual IEEE Communications Society Conference on, pp. 335-341. Oct. 2004.
Brown, B.H. et al., "Bipolar and Tetrapolar transfer impedance measurements from volume conductor," Electronics Letters, vol. 35, No. 25, 2000, pp. 2060-2062.
Cooley, W.L. et al., "A new design for an impedance pneumograph," Journal of Applied Physiology, vol. 25, No. 4, 1968, pp. 429-432.
Grenvik, A. et al., "Impedance Pneumography," Chest, vol. 62, No. 4, Oct. 1972, pp. 439-443.
Holt, T. et al., "Monitoring and recording of physiological data of the manned space flight program," Supplement to IEEE Transactions on Aerospace, Jun. 1965, p. 341-344.
Miller, Matthew J., et al., "On-Demand TDMA Scheduling for Energy Conservation in Sensor Networks," Technical Report, Jun. 2004.
Murat, B., "Electrical Impedance Plethysmography," Wiley Encyclopedia of Biomedical Engineering, 2006, p. 1-10.
NPL_VitalSense_2006, p. 1-2.
Poon, C. S. et al., "Evaluation of two noninvasive techniques for exercise ventilatory measurements," IEEE Engineering in Medicine and Biology conference, 1988, pp. 0823-0824.
Shakian, A. V. et al., "Electrode Motion Artifacts in Electrical Impedence Pneumography," IEEE Transactions in Biomedical Engineering, vol. BME-32, No. 6, Jun. 1985, pp. 448-451.

\* cited by examiner

SYSTEM AND METHOD FOR CONSERVING BATTERY POWER IN A PATIENT MONITORING SYSTEM

CROSS-REFERENCE TO RELATED APPLICATIONS

The following applications disclose certain common subject matter with the present application: A Vital-Signs Monitor with Encapsulation Arrangement, Ser. No. 12/844,766; A Vital-Signs Monitor with Spaced Electrodes, Ser. No. 12/844,769; A Vital-Signs Patch Having a Strain Relief, Ser. No. 12/844,774; A Temperature Probe Suitable for Axillary Reading, Ser. No. 12/844,775; System and Method for Monitoring Body Temperature of a Person, Ser. No. 12/844,771; A System and Method for Storing and Forwarding Data from a Vital-Signs Monitor, Ser. No. 12/844,780; System and Method for Saving Battery Power in a Vital Signs Monitor, Ser. No. 12/844,789; A System and Method for Saving Battery Power in a Patient Monitoring System, Ser. No. 12/844,801; A System And Method for Tracking Vital-Signs Monitor Patches, Ser. No. 12/844,788; A System And Method for Reducing False Alarms Associated with Vital-Signs Monitoring, Ser. No. 12/844,794; A System And Method for Location Tracking of Patients in a Vital-Signs Monitoring System, Ser. No. 12/844,781; A System And Method for Reducing False Alarms Based on Motion and Location Sensing, Ser. No. 12/844,765; all of the listed applications filed on Jul. 27, 2010.

BACKGROUND

Field

The present disclosure generally relates to systems and methods of physiological monitoring, and, in particular, relates to monitoring of vital signs of patients in hospitals.

Description of the Related Art

Some of the most basic indicators of a person's health are those physiological measurements that reflect basic body functions and are commonly referred to as a person's "vital signs." The four measurements commonly considered to be vital signs are body temperature, pulse rate, blood pressure, and respiratory rate. Some clinicians consider oxygen saturation ($S_{O2}$) to be a "fifth vital sign" particularly for pediatric or geriatric cases. Some or all of these measurements may be performed routinely upon a patient when they arrive at a healthcare facility, whether it is a routine visit to their doctor or arrival at an Emergency Room (ER).

Vital signs are frequently taken by a nurse using basic tools including a thermometer to measure body temperature, a sphygmomanometer to measure blood pressure, and a watch to count the number of breaths or the number of heart beats in a defined period of time which is then converted to a "per minute" rate. If a patient's pulse is weak, it may not be possible to detect a pulse by hand and the nurse may use a stethoscope to amplify the sound of the patient's heart beat so that she can count the beats. Oxygen saturation of the blood is most easily measured with a pulse oximeter.

When a patient is admitted to a hospital, it is common for vital signs to be measured and recorded at regular intervals during the patient's stay to monitor their condition. A typical interval is 4 hours, which leads to the undesirable requirement for a nurse to awaken a patient in the middle of the night to take vital sign measurements.

When a patient is admitted to an ER, it is common for a nurse to do a "triage" assessment of the patient's condition that will determine how quickly the patient receives treatment. During busy times in an ER, a patient who does not appear to have a life-threatening injury may wait for hours until more-serious cases have been treated. While the patient may be reassessed at intervals while awaiting treatment, the patient may not be under observation between these reassessments.

Measuring certain vital signs is normally intrusive at best and difficult to do on a continuous basis. Measurement of body temperature, for example, is commonly done by placing an oral thermometer under the tongue or placing an infrared thermometer in the ear canal such that the tympanic membrane, which shared blood circulation with the brain, is in the sensor's field of view. Another method of taking a body temperature is by placing a thermometer under the arm, referred to as an "axillary" measurement as axilla is the Latin word for armpit. Skin temperature can be measured using a stick-on strip that may contain panels that change color to indicate the temperature of the skin below the strip.

Measurement of respiration is easy for a nurse to do, but relatively complicated for equipment to achieve. A method of automatically measuring respiration is to encircle the upper torso with a flexible band that can detect the physical expansion of the rib cage when a patient inhales. An alternate technique is to measure a high-frequency electrical impedance between two electrodes placed on the torso and detect the change in impedance created when the lungs fill with air. The electrodes are typically placed on opposite sides of one or both lungs, resulting in placement on the front and back or on the left and right sides of the torso, commonly done with adhesive electrodes connected by wires or by using a torso band with multiple electrodes in the strap.

Measurement of pulse is also relatively easy for a nurse to do and intrusive for equipment to achieve. A common automatic method of measuring a pulse is to use an electrocardiograph (ECG or EKG) to detect the electrical activity of the heart. An EKG machine may use 12 electrodes placed at defined points on the body to detect various signals associated with the heart function. Another common piece of equipment is simply called a "heart rate monitor." Widely sold for use in exercise and training, heart rate monitors commonly consist of a torso band, in which are embedded two electrodes held against the skin and a small electronics package. Such heart rate monitors can communicate wirelessly to other equipment such as a small device that is worn like a wristwatch and that can transfer data wirelessly to a PC.

Nurses are expected to provide complete care to an assigned number of patients. The workload of a typical nurse is increasing, driven by a combination of a continuing shortage of nurses, an increase in the number of formal procedures that must be followed, and an expectation of increased documentation. Replacing the manual measurement and logging of vital signs with a system that measures and records vital signs would enable a nurse to spend more time on other activities and avoid the potential for error that is inherent in any manual procedure.

SUMMARY

For some or all of the reasons listed above, there is a need to be able to continuously monitor the vital signs of patients in different settings within a hospital, healthcare facility, or other location where care is provided to a patient. In addition, it is desirable for this monitoring to be done with limited interference with a patient's mobility or interfering with their other activities.

Continuous monitoring implies that the sensors that measure the physiological characteristic of interest remain continuously in place on the patient. Use of a wireless device to monitor the patient implies that the device is battery powered and the operating lifetime of the device is limited by the size of the battery compared to the rate at which the device consumes power. As it is desirable to leave the monitor patch attached to the patient for an extended period of time, possibly several days or more, a large battery may be required to enable the device to operate continuously or the batteries may be replaced to enable a device with a short operating life to continue to be used after its batteries are exhausted. A large battery may be intrusive to the patient's activities and uncomfortable to wear over an extended period of time. Having to replace batteries requires additional effort by the nurse, negating some of the time-saving benefit of using a continuous monitor and potentially providing a penetration of the sealed housing which protects the electronics of the monitor patch.

One solution to the problem of providing continuous monitoring with a small device and without having to periodically replace the batteries of the device is to reduce the power consumption of the device and conserve the battery power. With low-power electronics, the components that consume the most power may be the transmitter and receiver. Reducing the amount of time that the transmitter and receiver must be on to transmit a given amount of information may have the greatest impact on power reduction. The present application discloses a method of minimizing the amount of time that the transmitter and receiver must be on by eliminating the need to try and transmit and receive on frequencies that have so much noise that the signals are corrupted or masked completely.

Embodiments of the patient monitoring system disclosed herein measure certain vital signs of a patient, which include respiratory rate, pulse rate, and body temperature, on a regular basis and compare these measurements to preset limits.

In certain embodiments of the disclosure, a vital-signs patch in a patient monitoring system is disclosed. The patch includes a housing configured to be attached to the skin of a patient, the housing containing a radio that can selectably transmit and receive on more than one frequency and a processor. The processor configures the radio to transmit and receive on a determined frequency based at least in part on the level of noise detected on the frequencies.

In certain embodiments of the disclosure, a bridge in a patient monitoring system is disclosed. The bridge includes a housing that contains a radio that can selectably transmit and receive on more than one frequency, a memory in which is stored a list of frequencies, and a processor. The processor configures the radio to transmit and receive on a determined frequency from the list of frequencies based on the level of noise detected on the frequencies.

In certain embodiments of the disclosure, a method of conserving battery power in a wireless vital-signs patch that is attached to a patient in a patient monitoring system is disclosed. The method includes the steps of selecting a first frequency to evaluate, configuring a radio that can be configured to transmit and receive on more than one frequency to operate at the selected frequency, listening on the selected frequency to determine the magnitude of the radio noise at the selected frequency, and comparing the magnitude of the radio noise to a threshold value. If the magnitude of the radio noise is greater than a threshold value, the selected frequency is used for continued operation. Alternately, a new frequency is selected and the steps of listening and comparing is repeated.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Periodic monitoring of patients in a hospital is desirable at least to ensure that patients do not suffer an un-noticed sudden deterioration in their condition or a secondary injury during their stay in the hospital. It is impractical to provide continuous monitoring by a clinician and cumbersome to connect sensors to a patient, which are then connected to a fixed monitoring instrument by wires. Furthermore, systems that sound an alarm when the measured value exceeds a threshold value may sound alarms so often and in situations that are not truly serious that such alarms are ignored by clinicians.

Measuring vital signs is difficult to do on a continuous basis. Accurate measurement of cardiac pulse, for example, can be done using an electrocardiograph (ECG or EKG) to detect the electrical activity of the heart. An EKG machine may use up to 12 electrodes placed at various points on the body to detect various signals associated with the cardiac function. Another common piece of equipment is termed a "heart rate monitor." Widely sold for use in exercise and physical training, heart rate monitors may comprise a torso band in which are embedded two electrodes held against the skin and a small electronics package. Such heart rate monitors can communicate wirelessly to other equipment such as a small device that is worn like a wristwatch and that can transfer data wirelessly to a personal computer (PC).

Monitoring of patients that is referred to as "continuous" is frequently periodic, in that measurements are taken at intervals. In many cases, the process to make a single measurement takes a certain amount of time, such that even back-to-back measurements produce values at an interval equal to the time that it takes to make the measurement. For the purpose of vital sign measurement, a sequence of repeated measurements can be considered to be "continuous" when the vital sign is not likely to change an amount that is of clinical significance within the interval between measurements. For example, a measurement of blood pressure every 10 minutes may be considered "continuous" if it is considered unlikely that a patient's blood pressure can change by a clinically significant amount within 10 minutes. The interval appropriate for measurements to be considered continuous may depend on a variety of factors including the type of injury or treatment and the patient's medical history. Compared to intervals of 4-8 hours for manual vital sign measurement in a hospital, measurement intervals of 30 minutes to several hours may still be considered "continuous."

Certain exemplary embodiments of the present disclosure include a system that comprises a vital-signs monitor patch that is attached to the patient, and a bridge that communicates with monitor patches and links them to a central server that processes the data, where the server can send data and alarms to a hospital system according to algorithms and protocols defined by the hospital.

The construction of the vital-signs monitor patch is described according to certain aspects of the present disclosure. As the patch may be worn continuously for a period of time that may be several days, as is described in the following disclosure, it is desirable to encapsulate the components of the patch such that the patient can bathe or shower and engage in their normal activities without degradation of the patch function. An exemplary configuration of the construction of the patch to provide a hermetically sealed enclosure about the electronics is disclosed.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

Figure 1:
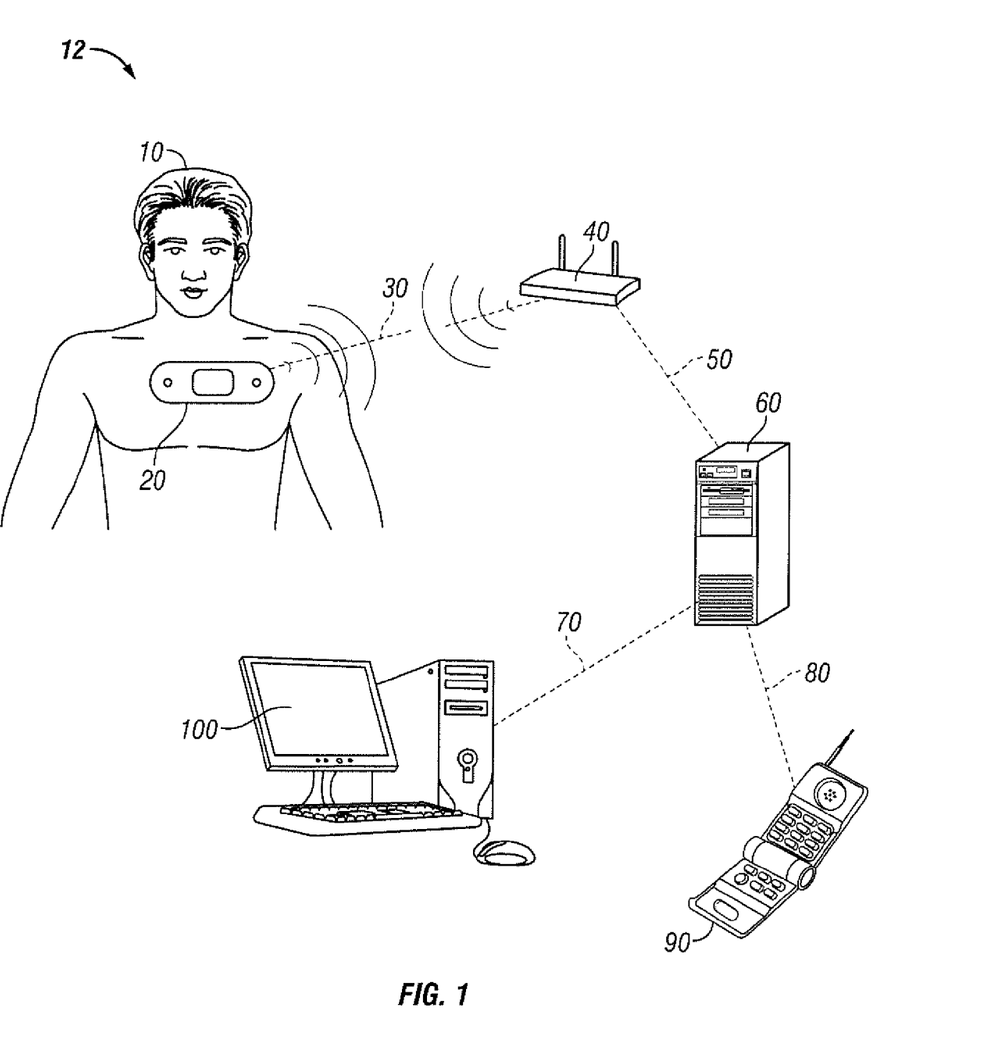
FIG. 1 is a diagram illustrating an exemplary embodiment of a patient monitoring system according to certain aspects of the present disclosure.

FIG. 1 discloses a vital sign monitoring system according to certain embodiments of the present disclosure. The vital sign monitoring system 12 includes vital-signs monitor patch 20, bridge 40, and surveillance server 60 that can send messages or interact with peripheral devices exemplified by mobile device 90 and workstation 100.

Monitor patch 20 resembles a large adhesive bandage and is applied to a patient 10 when in use. It is preferable to apply the monitor patch 20 to the upper chest of the patient 10 although other locations may be appropriate in some circumstances. Monitor patch 20 incorporates one or more electrodes (not shown) that are in contact with the skin of patient 10 to measure vital signs such as cardiac pulse rate and respiration rate. Monitor patch 20 also may include other sensors such as an accelerometer, temperature sensor, or oxygen saturation sensor to measure other characteristics associated with the patient. These other sensors may be internal to the monitor patch 20 or external sensors that are operably connected to the monitor patch 20 via a cable or wireless connection. Monitor patch 20 also includes a wireless transmitter that can both transmit and receive signals. This transmitter is preferably a short-range, low-power radio frequency (RF) device operating in one of the unlicensed radio bands. One band in the United States (US) is, for example, centered at 915 MHz and designated for industrial, scientific and medical (ISM) purposes. An example of an equivalent band in the European Union (EU) is centered at 868 MHz. Other frequencies of operation may be possible dependent upon the International Telecommunication Union (ITU), local regulations and interference from other wireless devices.

Surveillance server 60 may be a standard computer server connected to the hospital communication network and preferably located in the hospital data center or computer room, although other locations may be employed. The server 60 stores and processes signals related to the operation of the patient monitoring system 12 disclosed herein including the association of individual monitor patches 20 with patients 10 and measurement signals received from multiple monitor patches 20. Hence, although only a single patient 10 and monitor patch 20 are depicted in FIG. 1, the server 60 is able to monitor the monitor patches 20 for multiple patients 10.

Bridge 40 is a device that connects, or "bridges", between monitor patch 20 and server 60. Bridge 40 communicates with monitor patch 20 over communication link 30 operating, in these exemplary embodiments, at approximately 915 MHz and at a power level that enables communication link 30 to function up to a distance of approximately 10 meters. It is preferable to place a bridge 40 in each room and at regular intervals along hallways of the healthcare facility where it is desired to provide the ability to communicate with monitor patches 20. Bridge 40 also is able to communicate with server 60 over network link 50 using any of a variety of computer communication systems including hardwired and wireless Ethernet using protocols such as 802.11a/b/g or 802.3af. As the communication protocols of communication link 30 and network link 50 may be very different, bridge 40 provides data buffering and protocol conversion to enable bidirectional signal transmission between monitor patch 20 and server 60.

While the embodiments illustrated by FIG. 1 employ a bridge 20 to provide communication link between the monitor patch 20 and the server 60, in certain alternative embodiments, the monitor patch 20 may engage in direct wireless communication with the server 60. In such alternative embodiments, the server 60 itself or a wireless modem connected to the server 60 may include a wireless communication system to receive data from the monitor patch 20.

In use, a monitor patch 20 is applied to a patient 10 by a clinician when it is desirable to continuously monitor basic vital signs of patient 10 while patient 10 is, in this embodiment, in a hospital. Monitor patch 20 is intended to remain attached to patient 10 for an extended period of time, for example, up to 5 days in certain embodiments, limited by the battery life of monitor patch 20. In some embodiments, monitor patch 20 is disposable when removed from patient 10.

Server 60 executes analytical protocols on the measurement data that it receives from monitor patch 20 and provides this information to clinicians through external workstations 100, preferably personal computers (PCs), laptops, or smart phones, over the hospital network 70. Server 60 may also send messages to mobile devices 90, such as cell phones or pagers, over a mobile device link 80 if a measurement signal exceeds specified parameters. Mobile device link 80 may include the hospital network 70 and internal or external wireless communication systems that are capable of sending messages that can be received by mobile devices 90.

Figure 2A:
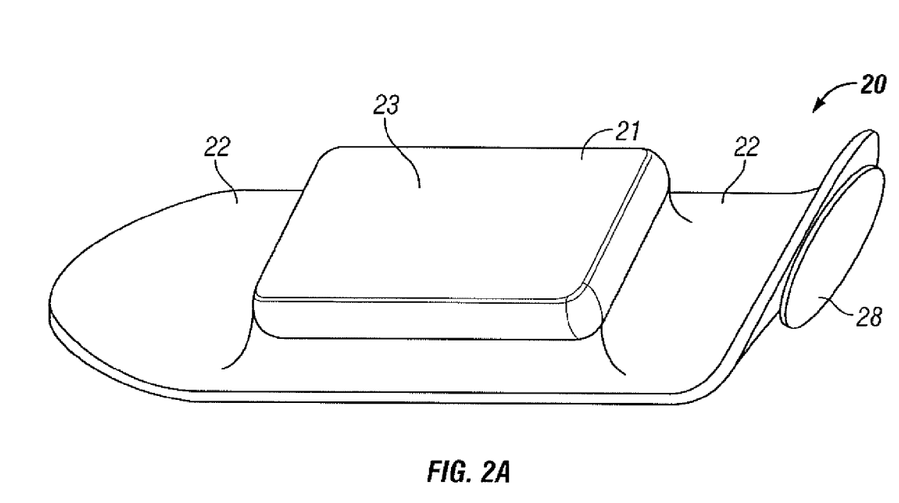
FIG. 2A is a perspective view of the vital signs patch of FIG. 1 according to certain aspects of the present disclosure.

FIG. 2A is a perspective view of the vital-signs monitor patch 20 shown in FIG. 1 according to certain aspects of the present disclosure. In the illustrated embodiment, the monitor patch 20 includes component carrier 23 comprising a central segment 21 and side segments 22 on opposing sides of the central segment 21. In certain embodiments, the central segment 21 is substantially rigid and includes a circuit assembly (24, FIG. 2B) having electronic components and battery mounted to a rigid printed circuit board (PCB). The side segments 22 are flexible and include a flexible conductive circuit (26, FIG. 2B) that connect the circuit assembly 24 to electrodes 28 disposed at each end of the monitor patch 20, with side segment 22 on the right shown as being bent upwards for purposes of illustration to make one of the electrodes 28 visible in this view.

Figure 2B:
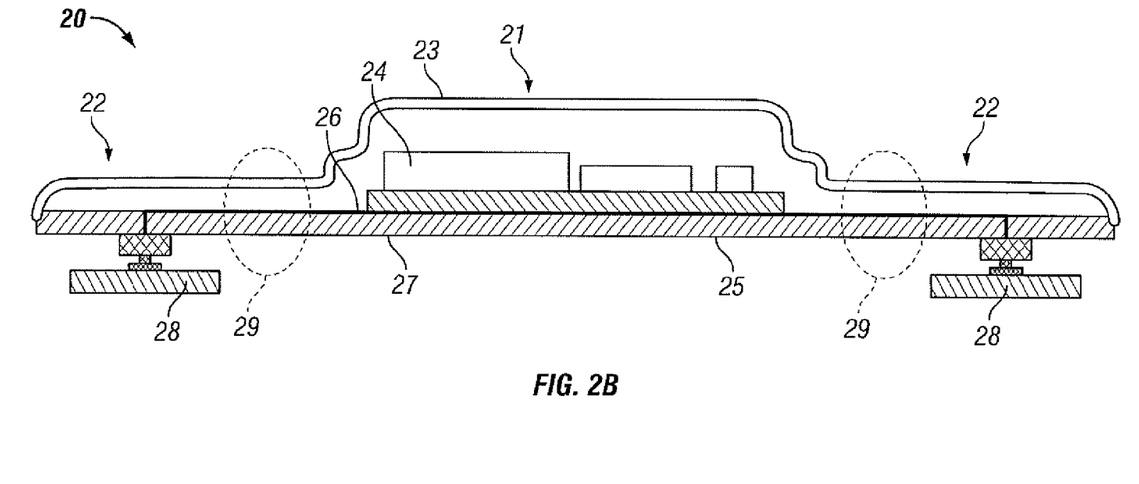
FIG. 2B is a cross-section of the vital signs patch of FIG. 1 according to certain aspects of the present disclosure.

FIG. 2B is a cross-sectional view of the vital-signs patch 20 shown in FIGS. 1 and 2A according to certain aspects of the present disclosure. The circuit assembly 24 and flexible conductive circuit 26 described above can be seen herein. The flexible conductive circuit 26 operably connects the circuit assembly 24 to the electrodes 28. Top and bottom layers 23 and 27 form a housing 25 that encapsulate circuit assembly 28 to provide a water and particulate barrier as well as mechanical protection. There are sealing areas on layers 23 and 27 that encircles circuit assembly 28 and is visible in the cross-section view of FIG. 2B as areas 29. Layers 23 and 27 are sealed to each other in this area to form a substantially hermetic seal. Within the context of certain aspects of the present disclosure, the term 'hermetic' implies that the rate of transmission of moisture through the seal is substantially the same as through the material of the layers that are sealed to each other, and further implies that the size of particulates that can pass through the seal are below the size that can have a significant effect on circuit assembly 24. Flexible conductive circuit 26 passes through portions of sealing areas 29 and the seal between layers 23 and 27 is maintained by sealing of layers 23 and 27 to flexible circuit assembly 28. The layers 23 and 27 are thin and flexible, as is the flexible conductive circuit 26, allowing the side segment 22 of the monitor patch 20 between the electrodes 28 and the circuit assembly 24 to bend as shown in FIG. 2A.

Figure 2C:
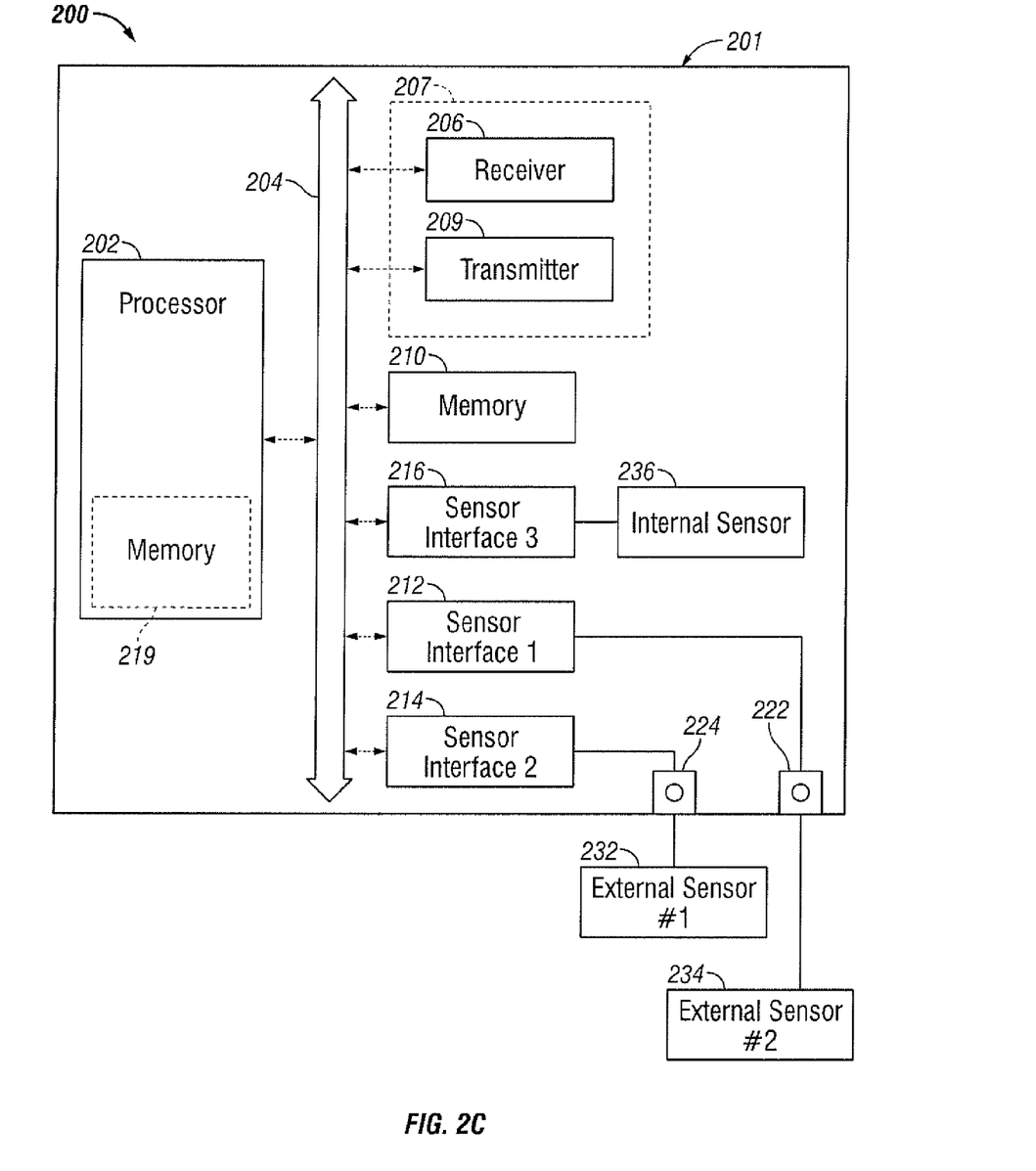
FIG. 2C is a functional block diagram illustrating exemplary electronic and sensor components of the monitor patch of FIG. 1 according to certain aspects of the present disclosure.

FIG. 2C is a functional block diagram 200 illustrating exemplary electronic and sensor components of the monitor patch 20 of FIG. 1 according to certain aspects of the present disclosure. The block diagram 200 shows a processing and sensor interface module 201 and external sensors 232, 234 connected to the module 201. In the illustrated example, the module 201 includes a processor 202, a wireless transceiver 207 having a receiver 206 and a transmitter 209, a memory 210, a first sensor interface 212, a second sensor interface 214, a third sensor interface 216, and an internal sensor 236 connected to the third sensor interface 216. The first and second sensor interfaces 212 and 214 are connected to the first and second external sensors 232, 234 via first and second connection ports 222, 224, respectively. In certain embodiments, some or all of the aforementioned components of the module 201 and other components are mounted on a PCB.

Each of the sensor interfaces 212, 214, 216 can include one or more electronic components that are configured to generate an excitation signal or provide DC power for the sensor that the interface is connected to and/or to condition and digitize a sensor signal from the sensor. For example, the sensor interface can include a signal generator for generating an excitation signal or a voltage regulator for providing power to the sensor. The sensor interface can further include an amplifier for amplifying a sensor signal from the sensor and an analog-to-digital converter for digitizing the amplified sensor signal. The sensor interface can further include a filter (e.g., a low-pass or bandpass filter) for filtering out spurious noises (e.g., a 60 Hz noise pickup).

The processor 202 is configured to send and receive data (e.g., digitized signal or control data) to and from the sensor interfaces 212, 214, 216 via a bus 204, which can be one or more wire traces on the PCB. Although a bus communication topology is used in this embodiment, some or all communication between discrete components can also be implemented as direct links without departing from the scope of the present disclosure. For example, the processor 202 may send data representative of an excitation signal to the sensor excitation signal generator inside the sensor interface and receive data representative of the sensor signal from the sensor interface, over either a bus or direct data links between processor 202 and each of sensor interface 212, 214, and 216.

The processor 202 is also capable of communication with the receiver 206 and the transmitter 209 of the wireless transceiver 207 via the bus 204. For example, the processor 202 using the transmitter and receiver 209, 206 can transmit and receive data to and from the bridge 40. In certain embodiments, the transmitter 209 includes one or more of a RF signal generator (e.g., an oscillator), a modulator (a mixer), and a transmitting antenna; and the receiver 206 includes a demodulator (a mixer) and a receiving antenna which may or may not be the same as the transmitting antenna. In some embodiments, the transmitter 209 may include a digital-to-analog converter configured to receive data from the processor 202 and to generate a base signal; and/or the receiver 206 may include an analog-to-digital converter configured to digitize a demodulated base signal and output a stream of digitized data to the processor 202. In other embodiments, the radio may comprise a direct sequence radio, a software-defined radio, or an impulse spread spectrum radio.

The processor 202 may include a general-purpose processor or a specific-purpose processor for executing instructions and may further include a memory 219, such as a volatile or non-volatile memory, for storing data and/or instructions for software programs. The instructions, which may be stored in a memory 219 and/or 210, may be executed by the processor 202 to control and manage the wireless transceiver 207, the sensor interfaces 212, 214, 216, as well as provide other communication and processing functions.

The processor 202 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable device or a combination of devices that can perform calculations or other manipulations of information.

Information, such as program instructions, data representative of sensor readings, preset alarm conditions, threshold limits, may be stored in a computer or processor readable medium such as a memory internal to the processor 202 (e.g., the memory 219) or a memory external to the processor 202 (e.g., the memory 210), such as a Random Access Memory (RAM), a flash memory, a Read Only Memory (ROM), a Programmable Read-Only Memory (PROM), an Erasable PROM (EPROM), registers, a hard disk, a removable disk, or any other suitable storage device.

In certain embodiments, the internal sensor 236 can be one or more sensors configured to measure certain properties of the processing and sensor interface module 201, such as a board temperature sensor thermally coupled to a PCB. In other embodiments, the internal sensor 236 can be one or more sensors configured to measure certain properties of the patient 10, such as a motion sensor (e.g., an accelerometer) for measuring the patient's motion or position with respect to gravity.

The external sensors 232, 234 can include sensors and sensing arrangements that are configured to produce a signal representative of one or more vital signs of the patient to which the monitor patch 20 is attached. For example, the first external sensor 232 can be a set of sensing electrodes that are affixed to an exterior surface of the monitor patch 20 and configured to be in contact with the patient for measuring the patient's respiratory rate, and the second external sensor 234 can include a temperature sensing element (e.g., a thermocouple or a thermistor or resistive thermal device (RTD)) affixed, either directly or via an interposing layer, to skin of the patient 10 for measuring the patient's body temperature. In other embodiments, one or more of the external sensors 232, 234 or one or more additional external sensors can measure other vital signs of the patient, such as blood pressure, pulse rate, or oxygen saturation.

Figure 3A:
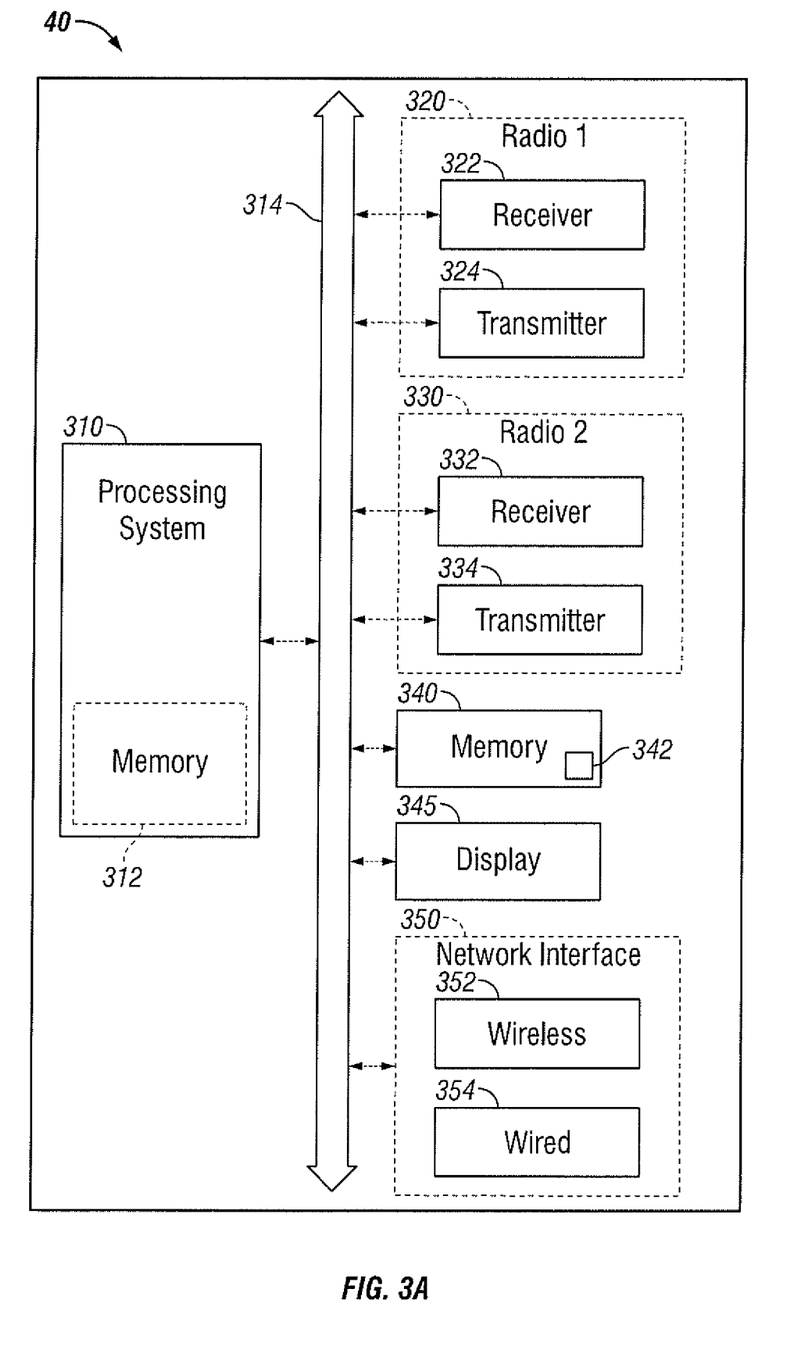
FIG. 3A is a functional schematic diagram of the bridge according to certain aspects of the subject disclosure.

FIG. 3A is a functional block diagram illustrating exemplary electronic components of bridge 40 of FIG. 1 according to certain aspects of the subject disclosure. Bridge 40 includes a processor 310, radio 320 having a receiver 322 and a transmitter 324, radio 330 having a receiver 332 and a transmitter 334, memory 340, display 345, and network interface 350 having a wireless interface 352 and a wired interface 354. In some embodiments, some or all of the aforementioned components of module 300 may be integrated into single devices or mounted on PCBs.

Processor 310 is configured to send data to and receive data from receiver 322 and transmitter 324 of radio 320, receiver 332 and transmitter 334 of radio 330 and wireless interface 352 and wired interface 354 of network interface 350 via bus 314. In certain embodiments, transmitters 324 and 334 may include a radio frequency signal generator (oscillator), a modulator, and a transmitting antenna, and the receivers 322 and 332 may include a demodulator and antenna which may or may not be the same as the transmitting antenna of the radio. In some embodiments, transmitters 324 and 334 may include a digital-to-analog converter configured to convert data received from processor 310 and to generate a base signal, while receivers 322 and 332 may include analog-to-digital converters configured to convert a demodulated base signal and sent a digitized data stream to processor 310.

Processor 310 may include a general-purpose processor or a specific-purpose processor for executing instructions and may further include a memory 312, such as a volatile or non-volatile memory, for storing data and/or instructions for software programs. The instructions, which may be stored in memories 312 or 340, may be executed by the processor 310 to control and manage the transceivers 320, 330, and 350 as well as provide other communication and processing functions.

Processor 310 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable device or a combination of devices that can perform calculations or other manipulations of information.

Information such as data representative of sensor readings may be stored in memory 312 internal to processor 310 or in memory 340 external to processor 310 which may be a Random Access Memory (RAM), flash memory, Read Only Memory (ROM), Programmable Read Only Memory (PROM), Erasable Programmable Read Only Memory (EPROM), registers, a hard disk, a removable disk, a Solid State Memory (SSD), or any other suitable storage device.

Memory 312 or 340 can also store a list or a database of established communication links and their corresponding characteristics (e.g., signal levels) between the bridge 40 and its related monitor patches 20. In the illustrated example of FIG. 3A, the memory 340 external to the processor 310 includes such a database 342; alternatively, the memory 312 internal to the processor 310 may include such a database.

Figure 3B:
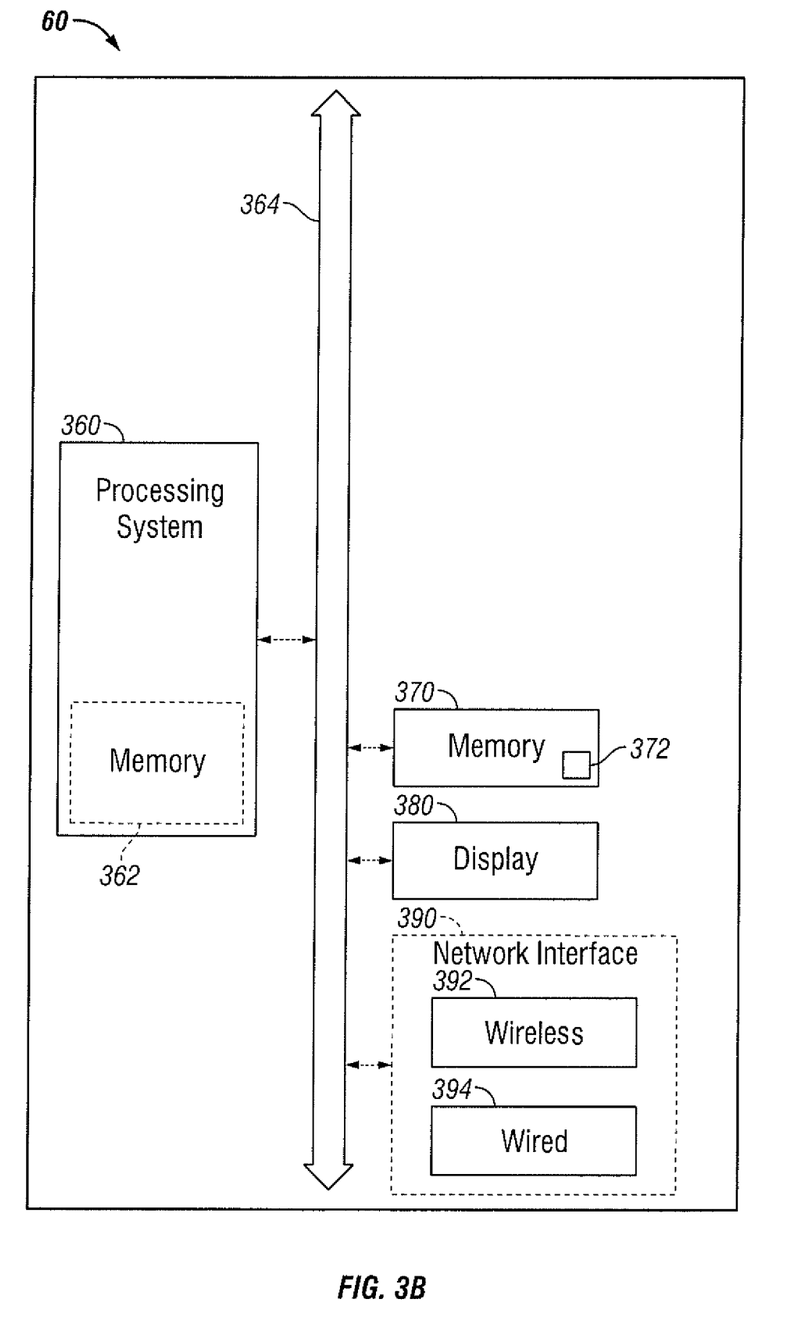
FIG. 3B is a functional schematic diagram of an embodiment of the surveillance server according to certain aspects of the present disclosure.

FIG. 3B is a functional block diagram illustrating exemplary electronic components of server 60 of FIG. 1 according to one aspect of the subject disclosure. Server 60 includes a processor 360, memory 370, display 380, and network interface 390 having a wireless interface 392 and a wired interface 394. Processor 360 may include a general-purpose processor or a specific-purpose processor for executing instructions and may further include a memory 362, such as a volatile or non-volatile memory, for storing data and/or instructions for software programs. The instructions, which may be stored in memories 362 or 370, may be executed by the processor 360 to control and manage the wireless and wired network interfaces 392, 394 as well as provide other communication and processing functions.

Processor 360 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable device or a combination of devices that can perform calculations or other manipulations of information.

Information such as data representative of sensor readings may be stored in memory 362 internal to processor 360 or in memory 370 external to processor 360 which may be a Random Access Memory (RAM), flash memory, Read Only Memory (ROM), Programmable Read Only Memory (PROM), Erasable Programmable Read Only Memory (EPROM), registers, a hard disk, a removable disk, a Solid State Memory (SSD), or any other suitable storage device.

Memory 362 or 370 can also store a database of communication links and their corresponding characteristics (e.g., signal levels) between monitor patches 20 and bridges 40. In the illustrated example of FIG. 3B, the memory 370 external to the processor 360 includes such a database 372; alternatively, the memory 362 internal to the processor 360 may include such a database.

Figure 4A:
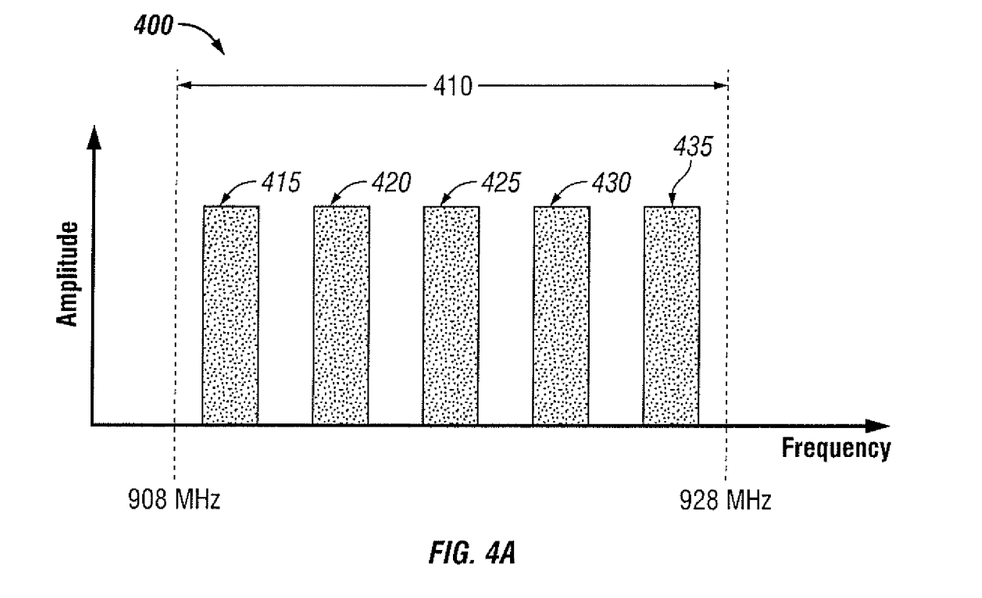
FIGS. 4A and 4B are frequency plots that show the subchannel frequencies at which the patch and bridge can communicate according to certain aspects of the subject disclosure.

FIG. 4A discloses an example of how subchannels may be defined within a radio frequency band according to certain aspects of the subject disclosure. Frequency plot 400 shows an example where the radio frequency band of interest is the ISM band 410 that has a center frequency of 915 MHz. The band covers the frequency range from 908 MHz to 928 MHz, resulting in a bandwidth of 20 MHz. In this example, five subchannels have been defined with center frequencies of 910 MHz, 914 MHz, 918 MHz, 922 MHz, and 926 MHz, designed as 415, 420, 425, 430, and 435 respectively. Each subchannel has a bandwidth of 2 MHz with 1 MHz of buffer on each side, resulting in a gap between subchannel bands of 2 MHz and a 1 MHz gap between the outer subchannel bands 415 and 435 and the limits of ISM band 410. It will be obvious that these subchannels can be created with other center frequencies and bandwidths to create other configurations of subchannels. Subchannels do not have to be evenly spaced, nor do they have to have identical bandwidth, and there is no requirement that there be a gap between channels.

Figure 4B:
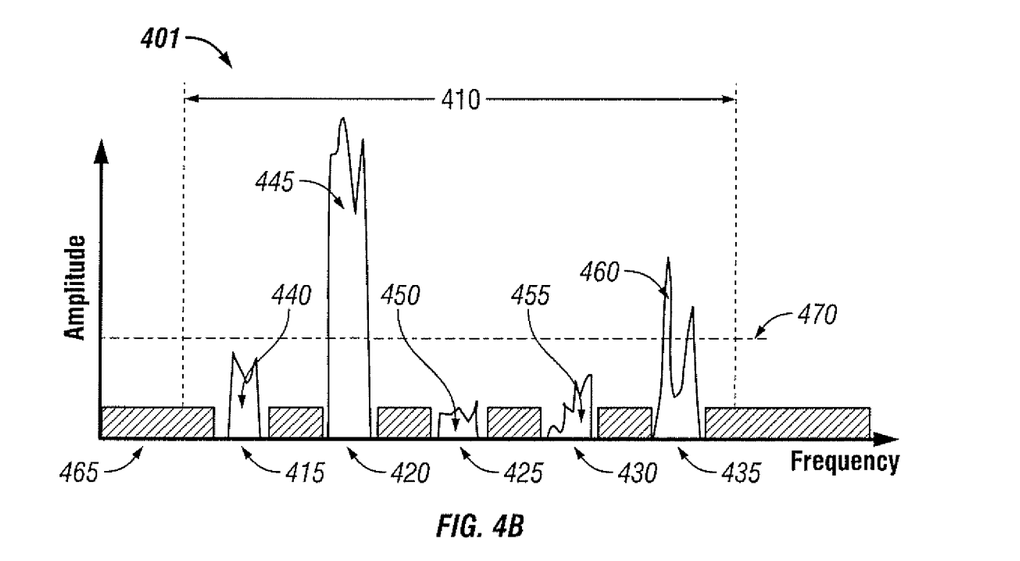

FIG. 4B discloses a frequency plot that illustrates the manner in which the subchannel frequencies are used by the patch and bridge to communicate according to certain aspects of the subject disclosure. Subchannels 415, 420, 425, 430, and 435 are defined as in FIG. 4A and are shown graphically as 'windows' along the horizontal frequency axis. The cross-hatched bar segments 465 along the frequency axis indicates frequencies that are not used. In this example, patch 20 and bridge 40 both have lists of the defined subchannel center frequencies stored in their respective memories and are configured to transmit within a 2 MHz bandwidth at each frequency.

In some embodiments, patch 20 consumes a relatively larger amount of battery power while transmitting than while listening, making it advantageous to transmit only when it is likely that the signal will be received intact by a bridge 40. In other embodiments, the rate of power consumption may be the same when listening and when transmitting. To conserve battery power, patch 20 listens at the first frequency on its stored list of frequencies and measures the amount of radio noise. Frequency plot 401 displays the amplitude of radio signals on its vertical axis. A threshold value has been predetermined as to the maximum acceptable radio noise on a subchannel. This threshold value is shown as 470 on plot 401. If the radio noise exceeds this threshold value, it is considered unacceptable to use this subchannel. Patch 20 will not attempt to contact a bridge on this subchannel.

In this example, subchannel 420 is the first frequency on the patch's stored list of frequencies. FIG. 4B shows that within the bandwidth of subchannel 420 there is radio noise 445 that has an amplitude that exceeds threshold value 470. The patch 20 will reject subchannel 420 and select another frequency (subchannel) to evaluate. In this example, subchannel 425 is next on the stored list of frequencies. In this example, there is noise 450 within the bandwidth of subchannel 425 and the amplitude of noise 450 is below threshold value 470. Patch 20 will now transmit a signal on subchannel 425 to establish communication with a nearby bridge 40. By transmitting only when the subchannel has been confirmed to be clear of radio noise below threshold value 470, patch 20 conserves its battery power.

If a bridge 40 responds on subchannel 425, this subchannel will continue to be used for future communication between this patch 20 and this bridge 40 as the low noise make it likely that signals will not be lost which would require retransmission by the patch 20 or by bridge 40, reducing the overall consumption of battery power in patch 20.

Bridge 40 uses a similar technique to select its operating subchannel. By operating on a clear subchannel, bridge 40 enables patch 20 to transmit to bridge 40 without interference, eliminating retransmission. Bridge 40 selects a first subchannel frequency from its list. In this example, the first subchannel on the list of bridge 40 is subchannel 460. Bridge 40 listens on subchannel 460 and finds noise 460 that has an amplitude greater than threshold value 470. Bridge 40 rejects subchannel 460 and selects another subchannel to evaluate. In this example, the second subchannel on the list of bridge 40 is subchannel 430. As the amplitude of radio noise 455 is lower than the threshold value 470, bridge 40 selects subchannel 430 for continued operation.

To provide additional assurance that a frequency is clear before selecting it for continued use, bridge 40 may perform an active check after completion the passive listening check described in the previous paragraph. In the example above, after bridge 40 listens on a subchannel 430 and determines that the noise 455 is below threshold 470, bridge 40 can transmit a signal on subchannel 430 asking whether there is any other bridge 40 using this frequency. If there is a nearby second bridge 40 using this same subchannel that by random chance did not happen to broadcast while the first bridge 40 was listening but is within the broadcast range of the first bridge 40, the second bridge 40 will respond to this query. This response will identify that the two bridges 40 are close enough that they will interfere with each other if they both use the same subchannel. In this situation, the first bridge 40 can reject subchannel 430 and continue with its search for a clear subchannel.

Bridge 40 can also respond to changes in radio noise on the subchannel that the bridge 40 is using. To continue with the bridge example of the previous paragraph, if bridge 40 is communicating with a patch 20 on subchannel 430 and the radio noise increases such that messages are no longer being received without error or bridge 40 detects that messages from patch 20 are being lost, bridge 40 can initiate a search for a new operating frequency. Bridge 40 will select another frequency from its list and listen on that new frequency. In this continued example, bridge 40 evaluates subchannel 415 and finds that the amplitude of the noise is below the threshold value 470. Bridge 40 will switch back to subchannel 430 and send a command to patch 20 to switch to subchannel 415. After bridge 40 receives an acknowledgement from patch 20 that it received the command intact, bridge 40 will switch to subchannel 415, re-establish communication with patch 20, and continue normal operation on subchannel 415. The battery power of patch 20 is conserved by the elimination of retransmissions required by the noise on subchannel 430. Battery power is also conserved by the verification that subchannel 315 was acceptable before commanding patch 20 to switch frequencies, avoiding the need for the patch 20 to try transmitting on multiple new frequencies to verify that the channel is clear.

It can be seen that the disclosed embodiments of the vital-signs monitor patch provide a mobile solution to monitoring the vital signs of a patient. The design of the vital-signs monitor patch frees nurses, or other caregivers, from the task of repetitively measuring the vital signs of their patients, allowing the caregivers to spend more time on other duties. The ability to continuously monitor a patient's vital signs using a monitor patch, together with the rest of the patient monitoring system, increases the ability of the nurse to respond quickly to a sudden change in a patient's condition, resulting in improved care for the patient.

The system and method disclosed herein conserve battery power in the vital-signs monitor patch in certain embodiments by verifying that a communication channel is clear of noise which might corrupt or mask signals between the patch and the bridge, which might require the patch to transmit a particular data packet multiple times before the packet was received intact. Avoiding these multiple wasted communication attempts will reduce the amount of power consumed to transfer a given amount of information from the patch to the bridge. Reduction of power consumption in the vital-signs monitoring patch enables the patch to be smaller and lighter than it would be if the disclosed features were not utilized. Use of a smaller battery enables the entire patch to be smaller. A smaller patch will be more comfortable to wear and less intrusive in normal activities of the patient as well as less expensive to manufacture. Increased comfort by the user and reduced cost to the facility providing the care will result in an increased likelihood that the device will be used, resulting in improved patient safety.

The previous description is provided to enable any person skilled in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The term 'battery' is intended to encompass all energy storage devices which deliver electricity. These energy storage devices may be rechargeable or single-use. This includes but is not limited to batteries using lead-acid, zinc-carbon, alkaline, nickel cadmium, lithium, and lithium-ion technologies, capacitors, generators powered by springs or compressed gas or other mechanical energy storage mechanisms, and fuel cells.

Those of skill in the art will appreciate that the various illustrative functional bocks, modules, components, methods, and algorithms described herein may be implemented as hardware, software, or a combination of the two. Various components and functional elements may be arranged in a different configuration or partitioned in a different way without departing from the scope of the claimed invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A vital-signs patch in a patient monitoring system, the patch comprising:
   a patch housing configured for attaching to the skin of a patient and containing:
      a plurality of electrodes in contact with the skin of the patient to measure a plurality of physiological parameters of the patient;
      a radio configured to selectably transmit and receive on more than one frequency; and
      a processor operably connected to the radio, the processor:
         configuring a radio that can be configured to transmit and receive on more than one frequency to operate at a selected frequency, the selected frequency determined from a stored list of frequencies;
         listening on the selected frequency to determine an amplitude of radio noise at the selected frequency;
         comparing the amplitude of the radio noise to a threshold value;
         when the amplitude of the radio noise is greater than the threshold value, determining a new frequency from the stored list of frequencies and repeating the steps of configuring, listening and comparing at the new frequency prior to initiating transmission on the new frequency;
         when the amplitude of the radio noise is below the threshold value, using the selected frequency for initiating the transmission to a receiving device; and
         switching the transmission to a selected other frequency in response to sending a confirmation of a command received on the selected frequency from the receiving device that commands the processor to switch to the selected other frequency.

2. A method of conserving battery power in a wireless vital-signs patch that is attached to a patient in a patient monitoring system, comprising the steps of:
   configuring a radio that can be configured to transmit and receive on more than one frequency to operate at a selected frequency, the selected frequency determined from a stored list of frequencies;

listening on the selected frequency to determine an amplitude of radio noise at the selected frequency;

comparing the amplitude of the radio noise to a threshold value;

when the amplitude of the radio noise is greater than the threshold value, determining a new frequency from the stored list of frequencies and repeating the steps of configuring, listening and comparing at the new frequency prior to initiating transmission on the new frequency;

when the amplitude of the radio noise is below the threshold value, using the selected frequency for initiating the transmission to a patch in a patient monitoring system, the patch comprising a plurality of electrodes in contact with skin of a patient to measure a plurality of physiological parameters of the patient; and switching the transmission to a selected other frequency in response to sending a confirmation of a command received on the selected frequency from the receiving device that commands the processor to switch to the selected other frequency.

3. The method of claim 2 wherein the selected frequency is associated with subchannels within a frequency band defined by a regulatory body.

4. The method of claim 3 wherein the radio is configured to operate at each subchannel frequency with a bandwidth that is smaller than the width of the frequency band.

5. The method of claim 2 wherein the transmission comprises transmitting vital-sign information from the vital-signs patch to a bridge that is part of the patient monitoring system.

6. A bridge in a patient monitoring system, the bridge comprising:

a bridge housing containing:

at least one radio configured to selectably transmit and receive on more than one frequency; and a processor operably connected to the radio, the processor:

configuring a radio that can be configured to transmit and receive on more than one frequency to operate at a selected frequency, the selected frequency determined from a stored list of frequencies;

listening on the selected frequency to determine an amplitude of radio noise at the selected frequency;

comparing the amplitude of the radio noise to a threshold value;

when the amplitude of the radio noise is greater than the threshold value, determining a new frequency from the stored list of frequencies and repeating the steps of configuring, listening and comparing at the new frequency prior to initiating transmission on the new frequency; and using the selected frequency for initiating the transmission to a patch in a patient monitoring system when the amplitude of the radio noise is below the threshold value, the patch comprising a plurality of electrodes in contact with skin of a patient to measure a plurality of physiological parameters of the patient; and switching to transmitting to the patch using another selected frequency in response to an acknowledgement received from the patch that the patch received a command to switch to the another selected frequency.

7. The bridge of claim 6 wherein the bridge housing further comprises a memory operably connected to the processor and configured to store a list of frequencies, the processor configured to determine the frequency for configuring the radio at least in part by selecting the frequency from the list of frequencies.

8. The vital-signs patch of claim 6 wherein the patch further comprises a memory operably connected to the processor and configured to store a list of frequencies; the processor configured to determine the frequency for configuring the radio at least in part by selecting the frequency from the list of frequencies.

9. The bridge of claim 6 wherein after selecting a frequency for the transmission, the processor is configured to send a command via the radio to a patch to use the frequency for communicating with the bridge.

10. The bridge of claim 6 wherein the more than one frequencies comprise frequencies associated with subchannels within a frequency band defined by a regulatory body.

11. The bridge of claim 10 wherein the bandwidth of each subchannel is smaller than the width of the frequency band.

12. The vital-signs patch of claim 6 wherein the more than one frequency comprise frequencies associated with subchannels within a frequency band defined by a regulatory body.

13. The vital-signs patch of claim 12 wherein the bandwidth of each subchannel is smaller than the width of the frequency band.

* * * * *